(12) United States Patent
Ogle et al.

(10) Patent No.: US 10,279,144 B2
(45) Date of Patent: May 7, 2019

(54) METHOD OF MANUFACTURING A CATHETER SHEATH

(71) Applicant: CathRx Ltd, Homebush Bay, NSW (AU)

(72) Inventors: David Ogle, Cowan (AU); Matthew J. Partlett, Allawah (AU); Garrett Ryan, Surry Hills (AU)

(73) Assignee: CathRx Ltd, Homebush Bay (AU)

( * ) Notice: Subject to any disclaimer, the term of this patent is extended or adjusted under 35 U.S.C. 154(b) by 0 days.

(21) Appl. No.: 15/645,224

(22) Filed: Jul. 10, 2017

(65) Prior Publication Data
US 2017/0354798 A1 Dec. 14, 2017

Related U.S. Application Data

(63) Continuation of application No. 13/816,729, filed as application No. PCT/AU2011/001010 on Aug. 12, 2011, now Pat. No. 9,700,696.
(Continued)

(51) Int. Cl.
*A61M 25/00* (2006.01)
*A61B 18/14* (2006.01)

(52) U.S. Cl.
CPC .... *A61M 25/0043* (2013.01); *A61M 25/0009* (2013.01); *A61M 25/0012* (2013.01);
(Continued)

(58) Field of Classification Search
CPC .... C07K 14/205; C12Q 1/6883; C12Q 1/689; C12Q 2600/158; G01N 2333/205;
(Continued)

(56) References Cited

U.S. PATENT DOCUMENTS 4,085,185 A    4/1978  Adair
4,592,372 A    6/1986  Beranek
(Continued)

FOREIGN PATENT DOCUMENTS

CN    201370879 Y    12/2009
DE      3038069 A1    4/1982
(Continued)

OTHER PUBLICATIONS

Chinese First Office Action for Chinese Application No. 201180037318.1 dated Jun. 5, 2014, 15 pages.
(Continued)

*Primary Examiner* — Imani N Hayman
(74) *Attorney, Agent, or Firm* — TraskBritt

(57) ABSTRACT

A catheter sheath comprises a tubular member connected to a catheter handle, the tubular sheath including one or more electrical conductors and one or more electrode rings attached to the tip of the tubular member. The tubular member further includes at least one opening that allows the one or more electrical conductor to be electrically connected to the one or more electrode rings. The electrode ring is slid over the tubular member so as to cover the opening. The tubular member and the electrode ring are subjected to heat treatment by induction heating so that the material of the tubular member melts locally around the electrode ring to form a seal between the tubular member and the electrode ring.

13 Claims, 7 Drawing Sheets

Related U.S. Application Data

(60) Provisional application No. 61/409,006, filed on Nov. 1, 2010, provisional application No. 61/373,725, filed on Aug. 13, 2010.

(52) U.S. Cl.
CPC ...... *A61B 18/1492* (2013.01); *A61M 25/0015* (2013.01); *Y10T 29/49117* (2015.01)

(58) Field of Classification Search
CPC ......... G01N 33/57446; A61B 18/1492; A61M 25/0009; A61M 25/0012; A61M 25/0015; A61M 25/0043; Y10T 29/49117
See application file for complete search history.

(56) References Cited

U.S. PATENT DOCUMENTS

| | | | |
|---|---|---|---|
| 5,029,585 | A | 7/1991 | Lieber et al. |
| 5,485,667 | A | 1/1996 | Kleshinski |
| 5,524,337 | A | 6/1996 | Houser et al. |
| 5,643,197 | A | 7/1997 | Brucker et al. |
| 5,792,140 | A | 8/1998 | Tu et al. |
| 5,895,355 | A | 4/1999 | Schaer |
| 5,913,856 | A | 6/1999 | Chia et al. |
| 6,144,870 | A | 11/2000 | Griffin, III |
| 6,430,426 | B2 | 8/2002 | Avitall |
| 6,562,021 | B1 | 5/2003 | Derbin et al. |
| 6,669,692 | B1 | 12/2003 | Nelson et al. |
| 8,517,999 | B2 | 8/2013 | Pappone et al. |
| 2002/0095202 | A1 | 7/2002 | Schmidt |
| 2007/0249923 | A1 | 10/2007 | Keenan |
| 2010/0168548 | A1 | 7/2010 | Govari et al. |
| 2011/0027127 | A1 | 2/2011 | Simpson et al. |

FOREIGN PATENT DOCUMENTS

| | | |
|---|---|---|
| EP | 0856292 A1 | 8/1998 |
| JP | 0839675 A | 2/1996 |
| JP | 09140802 A | 6/1997 |
| JP | 09140803 A | 6/1997 |
| JP | 2000202029 A | 7/2000 |
| JP | 2001000554 A | 1/2001 |
| JP | 2002517291 A | 6/2002 |
| JP | 2002224023 A | 8/2002 |
| JP | 3752402 A | 3/2006 |
| JP | 2007509693 A | 4/2007 |
| JP | 2007530155 A | 11/2007 |
| JP | 2008161240 B2 | 7/2008 |
| JP | 4242172 B2 | 3/2009 |
| JP | 2009268696 A | 11/2009 |
| WO | 96/18339 A1 | 6/1996 |
| WO | 98/49957 A1 | 11/1998 |
| WO | 2002045795 A2 | 6/2002 |
| WO | 2007100796 A2 | 9/2007 |
| WO | 2010011820 A4 | 1/2010 |
| WO | 2010028063 A2 | 3/2010 |
| WO | 2010063078 A1 | 6/2010 |

OTHER PUBLICATIONS

Chinese First Search for Chinese Application No. 201180037318.1 dated May 27, 2014, 2 pages.
International Preliminary Report on Patentability of International Application No. PCT/AU2011/001010, dated Feb. 19, 2013, 5 pages.
Search Report of International Application No. PCT/AU2011/001010, dated Nov. 15, 2011, 4 pages.
Written Opinion of International Application No. PCT/AU2011/001010, dated Nov. 15, 2011, 4 pages.
Japanese Notification of Reasons for Refusal for Japanese Application No. 2013-523435 dated Feb. 3, 2015, 11 pages.
Japanese Search Report for Japanese Application No. 2013-523435 dated Jan. 28, 2015, 40 pages.
European Search Report and Search Opinion Received for EP Application No. 11815901, dated Jun. 2, 2017, 7 pages.
Chinese Second Office Action for Chinese Application No. 201510812730.6, dated Aug. 28, 2018, 10 pages., Aug. 28, 2018.
Chinese Search Report for Chinese Application No. 201510812730.6, dated Mar. 20, 2018, 1 page., Mar. 20, 2018.

METHOD OF MANUFACTURING A CATHETER SHEATH

CROSS-REFERENCE TO RELATED APPLICATIONS

This application is a continuation of U.S. application Ser. No. 13/816,729, filed Feb. 12, 2013, now U.S. Pat. No. 9,700,696, issued Jul. 11, 2017, which is a national phase entry under 35 U.S.C. § 371 of International Patent Application PCT/AU2011/001010, filed Aug. 12, 2011, designating the United States of America and published in English as International Patent Publication WO 2012/019225 A1 on Feb. 16, 2012, which claims the benefit under Article 8 of the Patent Cooperation Treaty and under 35 U.S.C. § 119(e) to U.S. Provisional Patent Application Ser. Nos. 61/373,725, filed Aug. 13, 2010, and 61/409,006, filed Nov. 1, 2010, the disclosure of each of which is hereby incorporated herein by this reference in its entirety.

TECHNICAL FIELD

This application relates to a catheter sheath and a method for manufacturing a catheter sheath. In particular, this application relates to a method for attaching an electrode to a catheter sheath of a catheter assembly.

BACKGROUND

Any discussion of the prior art throughout the specification should in no way be considered as an admission that such prior art is widely known or forms part of common general knowledge in the field.

Catheters are commonly used in medical practice to examine and treat the heart. They may be inserted into the cardiovascular system of the patient through small punctures in the skin. They may then extend through a vein into the heart where they sense the electrical activity of the heart. In certain types of aberrant electrical activity, some catheters may be able to treat the heart by ablating certain areas of the heart. Catheters typically include a tubular structure such as a plastic tube with one or more electrodes attached to the tip of the tube.

Many catheters use conductive metal rings as electrodes. These metal rings are positioned at various intervals along the length of the tip section of the tube. These types of ring electrodes may be used for various tasks including radiopaque markers, antennas, and sensors for sensing electrical signals. Typically, the rings are secured in place using an appropriate adhesive, or by some mechanical means such as crimping or swaging. Swaging is a process of reducing the diameter of a ductile metal tube to a smaller, predetermined diameter.

The problem with mechanical attachment is that it may allow fluid to pass between the ring and the tube. Biological fluid may then enter the tube, and may be trapped under the electrode ring or within the catheter.

An adhesive may be used to seal the region between the ring and the tube. The adhesive may also be applied to the margins or edges of the ring electrode to further improve the seal between the ring electrode and the catheter tube. The use of adhesives may, however, be problematic because particles of the resin may become detached from the catheter tube during use. This is undesirable as it presents a risk to the patient. In addition, the application process of the adhesive requires precision and makes the manufacturing process of the catheter slower and more expensive.

These problems are exacerbated for catheters that are reprocessed or reused. When a catheter tube is cleaned and sterilized after it has been used, the mechanical joint between the ring electrodes and the catheter tube may be weakened and biological matter may enter the catheter tube. Weakening of the joints and resulting failure can be particularly common after multiple reprocessing cycles. It is also possible for small particles of the adhesive to become detached during reprocessing leaving small cavities in the resin. These cavities may catch biological matter when the catheter is used, and the biological matter may, in turn, be transferred to another patient because these types of small cavities may be difficult to clean.

BRIEF SUMMARY

It is an object of the present invention to overcome or ameliorate at least one of the disadvantages of the prior art, or to provide a useful alternative.

According to the present invention, there is provided a method of manufacturing a catheter sheath including: providing a tubular member of non-conductive material having a proximal end and a distal end, the tubular member further having one or more electrical conductors extending from the proximal end to the distal end within the tubular member, forming at least one opening in an outer wall of the tubular member for accessing the at least one electrical conductor within the tubular member, and attaching at least one conductive element on the outer wall of the tubular member in conductive connection with the at least one electrical conductor so that the at least one conductive element is adjacent to and surrounding the opening, and treating the tubular member and the at least one conductive element with heat by induction heating so that the tubular member melts locally around the at least one conductive element to form a seal along each edge of the conductive element. The at least one conductive element may include a ring electrode that is a snug fit about the tubular member.

An embodiment of the invention provides that attaching the at least one conductive element on the tubular member is arranged by a radially applied force. The radially applied force may compress the at least one conductive element so that an outer surface of the at least one conductive element lies substantially flush with the outer wall of the tubular member. The radial force may include swaging.

According to an embodiment of the invention, a sacrificial heat-shrink over the at least one conductive element is applied during the heat treatment. A mold may alternatively be applied over the at least one conductive element during the heat treatment.

According to an embodiment of the invention, the one or more electrical conductors are arranged within a lumen defined by the tubular member. However, the one or more electrical conductors may also be arranged between inner and outer walls of the tubular member.

In a second aspect, there is provided a catheter sheath comprising: a tubular member of non-conductive material having a proximal end and a distal end, at least one electrical conductor extending from the proximal end to the distal end within the tubular member, at least one opening in an outer wall of the tubular member for accessing the at least one electrical conductor within the tubular member, and at least one conductive element on the outer wall of the tubular member, the at least one conductive element being adjacent to and surrounding the opening and arranged in conductive connection with the at least one electrical conductor, wherein the tubular member is arranged to form a seal along each edge of the at least one conductive element by heat treating the tubular member by induction heating so that the tubular member melts locally around the at least one conductive element. The at least one conductive element may be a ring electrode that is a snug fit about the tubular member.

According to an embodiment of the invention, the at least one conductive element is attached to the tubular member by a radially applied force. The radially applied force may be arranged to compress the at least one conductive element so that an outer surface of the at least one conductive element is substantially flush with the outer wall of the tubular member. The radially applied force may include swaging.

According to an embodiment of the invention, the seal is arranged by applying a sacrificial heat-shrink over the at least one conductive element during the heat treatment. The seal may also be arranged by applying a mold over the at least one conductive element during the heat treatment.

According to an embodiment of the invention, the at least one electrical conductor is arranged between an inner and outer wall of the tubular member. The at least one electrical connector may also be arranged longitudinally within a lumen defined by the tubular member.

BRIEF DESCRIPTION OF THE DRAWINGS

Preferred embodiments of the invention will now be described, by way of example only, with reference to the accompanying drawings in which.

DETAILED DESCRIPTION

Figure 1:
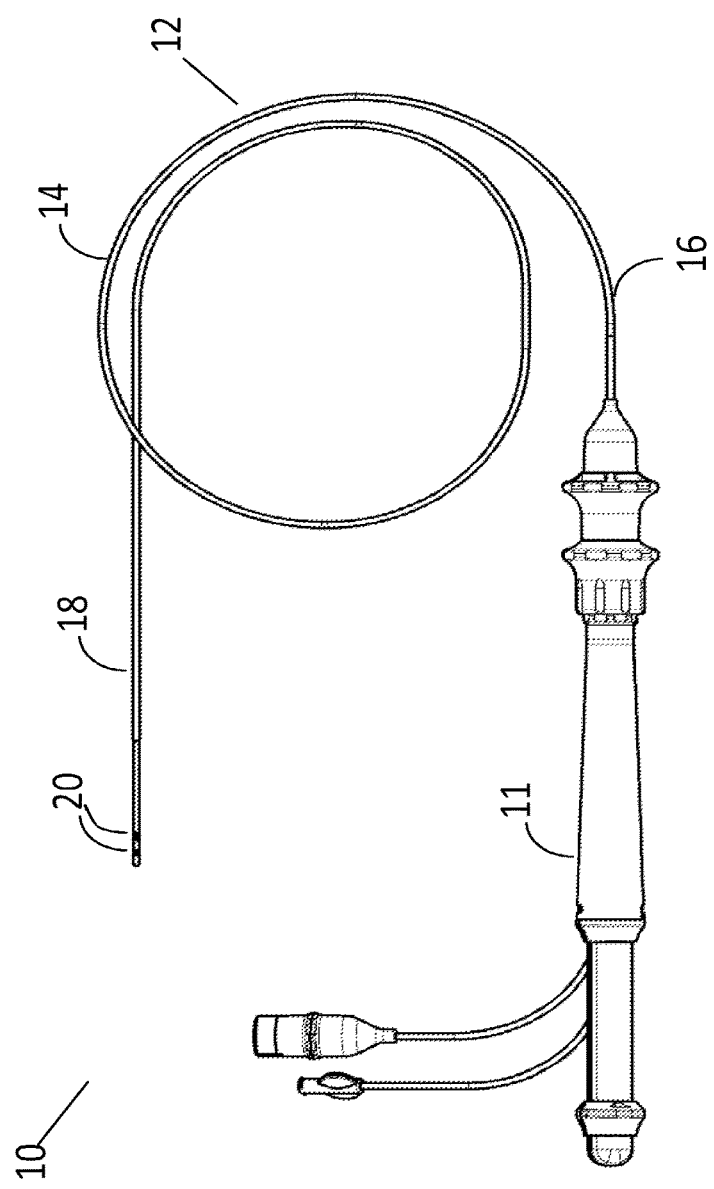
FIG. 1 shows a catheter assembly including an embodiment of a catheter sheath of the catheter assembly.

FIG. 1 depicts a heart catheter 10. The catheter includes a handle 11, and an elongate catheter sheath 12 extending from the handle 11. The catheter sheath 12 consists of a generally tubular member 14 having a proximal end 16 connected to the handle 11 and a distal end 18 having one or more electrodes 20 attached to the tubular member 14.

The electrodes 20 are in predetermined, axially spaced locations between the proximal end 16 and the distal end 18 of the tubular member 14. Although electrodes of different shapes may be used, an annular electrode ring 20 having an inside diameter equal to or greater than the outside diameter of the tubular member 14 is shown in the accompanying figures. The electrode ring 20 is preferably a platinum-iridium ring but may be made of other suitable conductive material. The inner diameter of each ring approximates the outer diameter of the tubular member 14 so that each ring electrode 20 is a snug fit about an external surface of the tubular member 14.

The tubular member 14 includes conductors (not shown in FIG. 1) that are connected to the electrodes 20 at the distal end 18 of the tubular member 14. The conductors are able to carry the signal sensed by the electrodes 20 through the tubular member 14 to the handle 11 where the conductors 30 further connect to electrical instruments, for example, to a monitor, a stimulator, or a source of energy such as an RF energy source used for ablation. At least one conductor may be associated with an electrode 20, but several conductors may be required for one electrode. The tubular member 14 is preferably formed of a biocompatible and resilient material that is non-conductive. Polymeric materials such as a polyether block amide (PEBAX), silicone or polyurethane may be used.

Figure 2A:
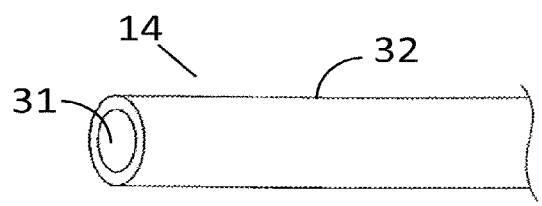
FIGS. 2a-2f are schematic views that show the steps of manufacturing a tubular member used in the method of manufacturing a catheter sheath.
Figure 2B:
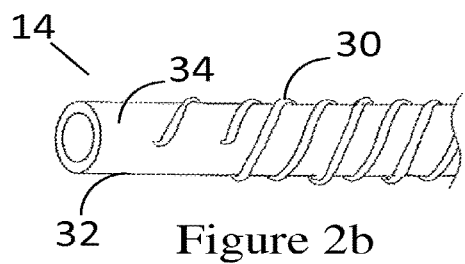
Figure 2C:
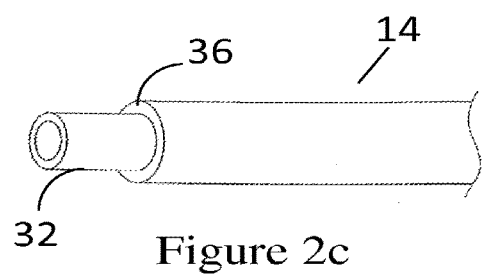

FIGS. 2a-2f are schematic views that show a close-up of the distal end 18 of the tubular member 14 as a series of figures illustrating the manufacturing process of the catheter member 14. In this embodiment, the tubular member 14 is initially formed by an inner tubular section 32 defining an elongate lumen 31 within the tubular member 14. A plurality of conductors 30, one of which is shown in FIG. 2b, is helically wound about an outer surface 34 of the inner tubular section 32. A coating 36 of a plastic material is laid over the conductors 30 to sandwich the conductors between the inner section 32 and the coating 36 as shown in FIG. 2c.

Figure 2D:
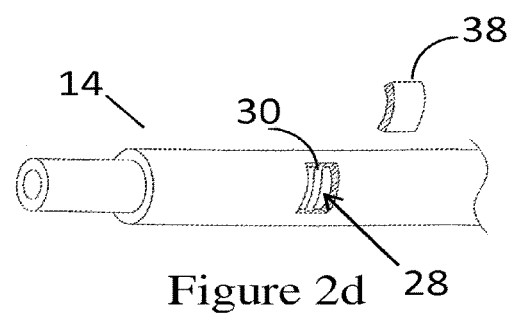
Figure 2E:
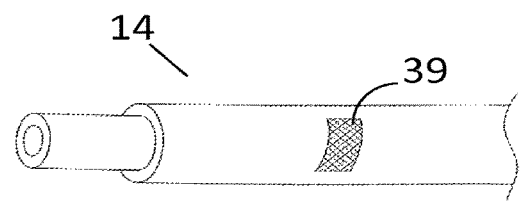
Figure 2F:
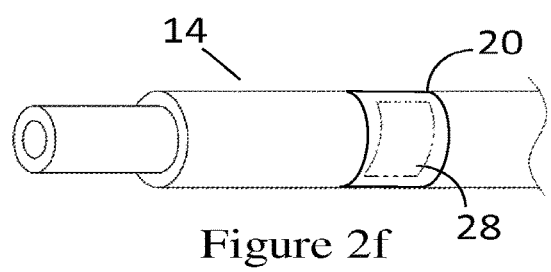

To attach one or more electrodes to the distal end 18 of the tubular member 14, an opening 28 is formed on the outer wall of the tubular member 14 as seen in FIG. 2d. The opening 28 is formed, for example, by laser cutting a portion 38 out of the tubular member 14. Laser cutting facilitates accurate cutting of the tubular member 14 and only the desired conductor or conductors 30 are revealed by cutting the portion 38 out of the tubular member. As seen in FIG. 2d, the opening 28 reveals one or more conductors 30 that are to be connected with an electrode 20. The opening 28 is filled with a suitable biocompatible adhesive 39 such as an epoxy adhesive as shown in FIG. 2e. The ring electrode is then slipped onto the tubular member to cover the opening 28 so that the ring electrode 20 is adjacent to and surrounding the opening 28 as seen in FIG. 2f. The epoxy adhesive 39 inserted into the opening is electrically conductive and, therefore, it ensures the conductive connection between the conductor 30 and the ring electrode 20.

Figure 3A:
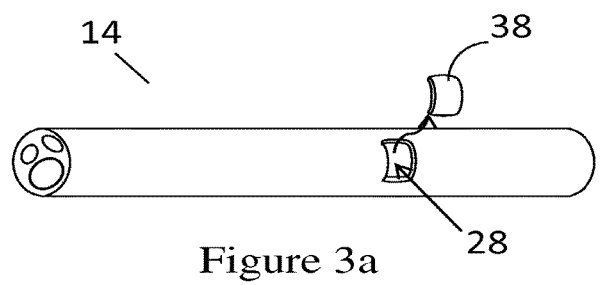
FIGS. 3a-3c are schematic views that illustrate the steps of manufacturing another type of tubular member used in the method of manufacturing a catheter sheath.
Figure 3B:
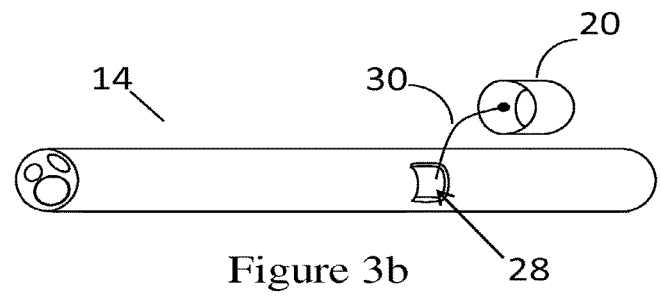
Figure 3C:
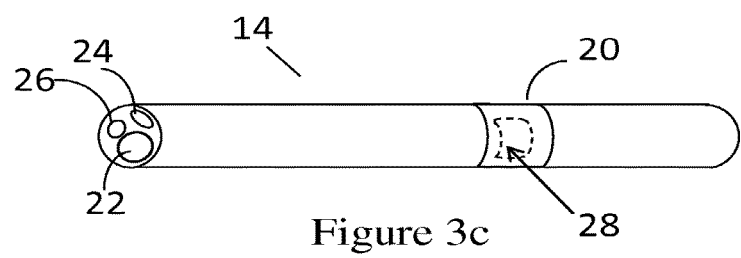

With reference to FIGS. 3a-3c, another type of tubular member is provided. The tubular member 14 in FIGS. 3a-3c defines one or more elongate passages, lumens, 22, 24 and 26 that extend longitudinally through the tubular member 14. The lumens can be used, for example, to house a deflection stylet for a deflection type catheter, or one or more electrical conductors 30 extending through the tubular member 14 from the distal end 18 of the tubular member to the proximal end 16 of the tubular member. In this type of catheter sheath 12, the conductors run longitudinally within one of the lumens 22, 24, 26. To attach one or more electrodes 20 to the distal end 18 of the tubular member 14, an opening 28 is formed on the outer wall of the tubular member 14 so that the conductor or conductors 30 may be drawn out of the tubular member to be connected to a respective electrode 20. The opening 28 extends from the lumen inside the tubular member 14 to the outside surface of the tubular member. As seen in FIG. 3b, the conductor or conductors 30 are preferably connected to the inner surface of the ring electrode 20. This conductive connection is provided by welding, soldering or any other suitable method. Induction welding is preferred as it provides a consistent result. No new materials need to be introduced when connecting the conductor 30 to the ring electrode 20 by induction welding, induction welding thus eliminating the need for any intermediate materials. With reference to FIG. 3c, once the conductor 30 is conductively connected to the electrode, the ring electrode 20 is slipped over the distal end 18 of the tubular member 14 to a position directly over the opening while drawing any excess length of the conductor 30 back into the lumen of the tubular member 14.

Once the ring electrode 20 is slipped onto the tubular member 14 adjacent to and surrounding the opening 28, it is then secured in place by heating and melting the tubular member around the electrode ring 20. Bonding of the electrode 20 to the tubular member 14 occurs as melted plastic of the tubular member 14 around the electrode ring 20 solidifies as it cools down. Most heating methods include an external heat source such as a hot air gun, or an oven. A method based on induction bonding has a number of advantages over these methods and it is, therefore, used to heat and melt the tubular member 14 surrounding the ring electrode 20 to form a seal between the electrode 20 and the opening 28. Induction heating can be used to heat, melt or solder an electrically conducting article such as the ring electrode 20. An induction heater used to treat the tubular member 14 consists typically of a power supply that provides a high frequency alternating current that is passed through a coil. The tubular member 14 with the electrode ring 20 attached onto it is inserted through the coil. Current is induced within the electrode ring placed in the coil, causing resistive heating of the metal ring 20. As the temperature of the ring electrode 20 increases, it melts the plastic tubular member 14 locally around the ring electrode 20 and bonds the two materials together. Induction heating is fast, clean and simpler to do than traditional methods to manufacture an electrode ring assembly. Depending on the size of the coil, induction heating allows targeted heating to relatively small areas and is particularly useful for heating or soldering elongated rod-like articles. During the heating process, mandrels may be inserted into the lumen of the catheter sheath to support the tubular member and inhibit the collapse or deformation of the tubular member 14.

FIGS. 4a and 4b, 5a and 5b, 6a and 6b, and 7a and 7b depict the tubular member 14 during the process of attaching the ring electrode or electrodes 20 onto the tubular member 14.

Figure 4A:
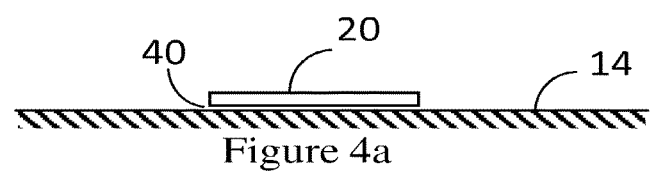
FIGS. 4a and 4b are schematic views that show a longitudinal cross-sectional side view of the tubular member with the ring electrode, before and after the heat treatment.
Figure 4B:
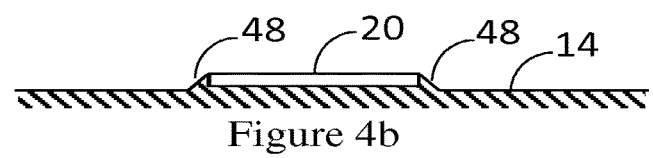

FIGS. 4a and 4b depict the connection between the electrode ring 20 and the tubular member 14 as a longitudinal cross-section through the tubular member 14 so that only one side of the connection between the electrode ring 20 and the tubular member 14 is shown. As the electrode ring 20 is slid onto the tubular member 14, a small gap 40 remains between the electrode ring 20 and the tubular member 14 as shown in FIG. 4a. This small gap 40 can be filled by locally heating and melting the plastic substrate of the tubular member 14 around the electrode ring 20 to form a seal between electrode ring 20 and the tubular member 14. FIG. 4b depicts the connection between the tubular member 14 and the electrode ring 20 after the sealing by induction heating has occurred. The tubular member 14 has melted around the ring and now forms a fillet 48 after cooling. This fillet 48 provides enhanced bond strength and helps to prevent biological material from being caught adjacent to the electrode 20.

The bond between the electrode ring 20 and the catheter tubular member 14 of the sheath 12 can be improved by swaging or another suitable mechanical compression method such as crimping (not shown in the accompanying drawings). Swaging is a process for shaping metallic articles such as rods, bars, or tubes. In particular, it can be used to reduce the diameter of such articles, or producing a taper in them. Once the ring electrode 20 has been slid into its place covering the opening 28, its diameter is reduced by swaging thus making the ring electrode tightly secure in its position on the tubular member 14. During swaging, the tubular member 14 with the electrode ring 20 is placed inside a die that applies compressive force by hammering and rotating around the ring. Alternatively, a mandrel can be inserted inside the tubular member during compression. Once the swaging process is complete, the outer diameter of the ring electrode 20 is substantially the same as the outer diameter of the tubular member 14.

Figure 5A:
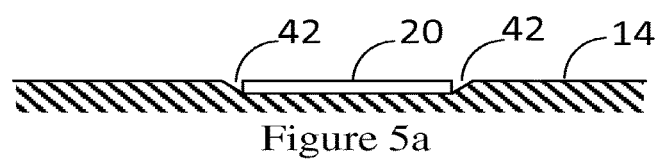
FIGS. 5a and 5b are schematic views that illustrate a longitudinal cross-sectional side view of the tubular member when the ring electrode is swaged onto the tubular member, before and after heat treatment.
Figure 5B:
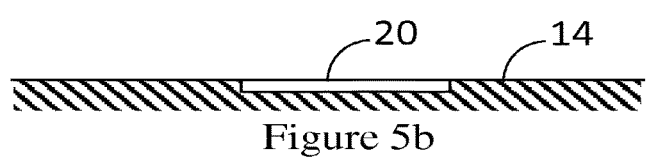

FIG. 5a shows in schematic view the connection between the tubular member 14 and the electrode ring 20 when the electrode ring 20 has been secured in its place by swaging. Swaging has reduced the diameter of the ring electrode 20 and the electrode 20 has been compressed into the tubular member 14 as can be seen in FIG. 5a. Although the electrode ring 20 has been compressed into the tubular member 14 of the sheath 12 so as to be flush with the sheath 12, a transition zone 42 remains adjacent to the ring electrode 20 where the plastic tubular member 14 has been compressed. The transition zone 42 runs circumferentially around the tubular member 14 in close proximity to the electrode ring 20. FIG. 5b shows the tubular member 14 and the electrode ring 20 after the tubular member 14 with the electrode ring 20 has been exposed to induction heating. The small transition zone 42 has been filled as the plastic material of the tubular member 14 has melted and solidified upon cooling tightly around the electrode ring 20. This provides a tight seal between the electrode ring 20 and the opening 28.

Figure 6A:
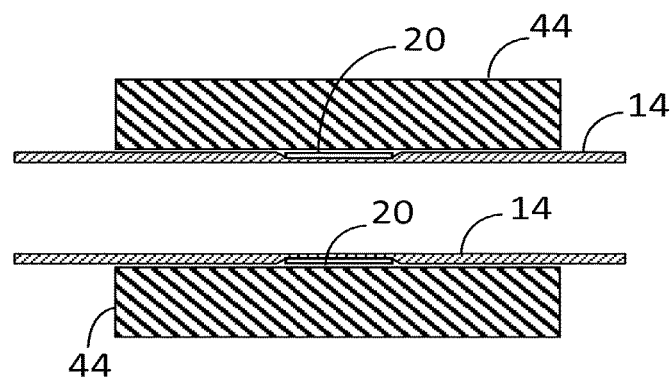
FIG. 6a shows a schematic side view of a step of attaching a ring electrode onto the catheter sheath by heat treating the sheath and using a die or a mold in the process of manufacturing a catheter sheath.
Figure 6B:
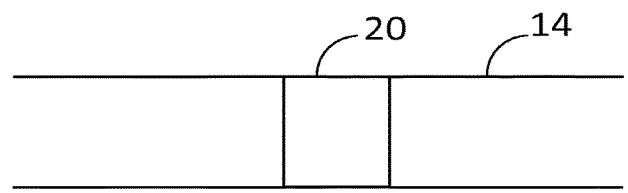
FIG. 6b shows a schematic side view of the distal end of the tubular member once the tubular member has been subjected to heat treatment by induction heating.

FIG. 6a shows in a schematic view a longitudinal cross-sectional view of the tubular member 14 with the electrode ring 20 swaged onto it. A mold or die 44 can further be used when manufacturing the catheter sheath 12 to ensure that the molten plastic of the tubular member 14 fills any gaps adjacent to the ring electrode 20. During the manufacturing process, the mold or die 44 covers the tubular member 14 and the electrode 20 so that upon melting and cooling, the surface of the ring becomes flush with the surface of the tubular member 14. As can be seen from FIG. 6b, the transition zone 42 formed during swaging is filled with the plastic of the tubular member 14 after the induction heating has been effected and the electrode ring 20 is flush with the outside surface of the tubular member 14.

Figure 7A:
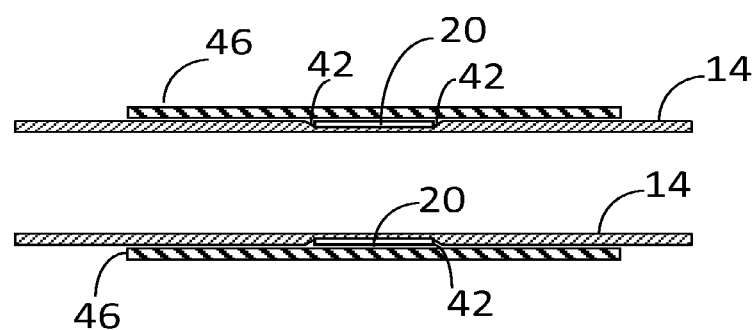
FIG. 7a shows a schematic side view of a step of attaching a ring electrode onto the tubular member by heat treating the sheath by induction heating and by using a heat-shrink to mold the sheath in the process of manufacturing a catheter sheath.
Figure 7B:
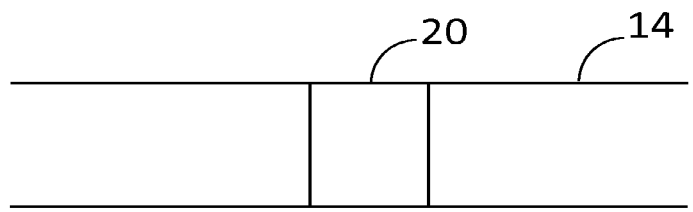
FIG. 7b shows a schematic side view of the distal end of the tubular member once the tubular member has been subjected to heat treatment by induction heating.

FIG. 7a shows the use of a sacrificial heat-shrink sleeve or other suitable tubing placed over the electrode ring 20. Upon heating, the electrode ring 20 conducts heat to the shrink sleeve, which in turn melts and molds the plastic tubular member 14 so that the outer surface of the electrode ring 20 is flush with the surface of the tubular member 14. It can be seen from FIG. 7b that the transition zone 42 formed during swaging (seen in FIG. 7a) has been filled with plastic after the bonding by induction heating has occurred. The distal end of the tubular member 14 is heated using a controlled heat source providing heating by induction. Heating of the tubular member 14 causes the material of the tubular member 14 to liquefy to an extent and to flow together causing closure of the transition zone 42. In addition, radial expansion of the tubular member material takes place, the extent of the radial expansion being constrained by the sleeve 46.

The advantage of the present catheter sheath and its manufacturing method is that it provides a tight seal between the electrode ring 20 and the tubular member 14, resulting in no fluid or other substance to be able to pass underneath the electrode ring. It is a further advantage that adhesion between the electrode ring and the tubular member 14 is enhanced without using any adhesives. Treating the tubular member 14 and the electrode ring 20 by induction heating further assures a smooth transition between the outer circumferential surface of the ring electrode 20 and the outer circumferential surface of the tubular member 14. It is a further advantage that the method of manufacturing of the catheter sheath simplifies the procedure of producing a suitable catheter sheath. In addition, the use of the induction heating technique to cause flow of the material of the tubular member 14 of the sheath 12 assists in sealing the tubular member 14 against the ingress of foreign material. This heating technique also serves to assist in retaining the electrodes in position on the catheter sheath and makes it thus more durable.

Reference throughout this specification to "one embodiment," "some embodiments" or "an embodiment" means that a particular feature, structure or characteristic described in connection with the embodiment is included in at least one embodiment of the present invention. Thus, appearances of the phrases "in one embodiment," "in some embodiments" or "in an embodiment" in various places throughout this specification are not necessarily all referring to the same embodiment, but may. Furthermore, the particular features, structures or characteristics in one or more embodiments may be combined in any suitable manner, as would be apparent to one of ordinary skill in the art from this disclosure.

As used herein, unless otherwise specified, the use of ordinal adjectives "first," "second," "third," etc., to describe a common object, merely indicate that different instances of like objects are referred to, and are not intended to imply that the objects so described must be in a given sequence, either temporally, spatially, in ranking, or in any other manner.

In the claims below and the description herein, any one of the terms "comprising," "comprised of," or "which comprises" is an open term that means including at least the elements/features that follow, but not excluding others. Thus, the term "comprising," when used in the claims, should not be interpreted as being limitative to the means or elements or steps listed thereafter. For example, the scope of the expression "a device comprising A and B" should not be limited to devices consisting only of elements A and B. Any one of the terms "including," "which includes" or "that includes," as used herein, is also an open term that also means including at least the elements/features that follow the term, but not excluding others. Thus, "including" is synonymous with and means "comprising."

It should be appreciated that in the above description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those skilled in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Similarly, it is to be noticed that the term coupled, when used in the claims, should not be interpreted as being limited to direct connections only. The terms "coupled" and "connected," along with their derivatives, may be used. It should be understood that these terms are not intended as synonyms for each other. Thus, the scope of the expression "a device A coupled to a device B" should not be limited to devices or systems wherein an output of device A is directly connected to an input of device B. It means that there exists a path between an output of A and an input of B, which may be a path including other devices or means. "Coupled" may mean that two or more elements are either in direct physical or electrical contact, or that two or more elements are not in direct contact with each other but yet still co-operate or interact with each other.

Thus, while there has been described what are believed to be the preferred embodiments of the invention, those skilled in the art will recognize that other and further modifications may be made thereto without departing from the spirit of the invention, and it is intended to claim all such changes and modifications as falling within the scope of the invention. For example, any formulas given above are merely representative of procedures that may be used. Functionality may be added or deleted from the block diagrams and operations may be interchanged among functional blocks. Steps may be added or deleted to methods described within the scope of the invention.

It will be appreciated by persons skilled in the art that numerous variations and/or modifications may be made to the disclosure as shown in the specific embodiments without departing from the scope of the disclosure as broadly described. The present embodiments are, therefore, to be considered in all respects as illustrative and not restrictive.

What is claimed is:

1. A method of manufacturing a catheter sheath, comprising:
   providing a tubular member of non-conductive material having a proximal end and a distal end;
   forming at least one opening in an outer wall of the tubular member;
   attaching at least one conductive element on the outer wall of the tubular member;
   placing a mold about the at least one conductive element and longitudinally adjacent the outer wall of the tubular member;

heating by induction the at least one conductive element in which the induction heat is directly conducted by only the at least one conductive element, such that indirect heat from the induction heated at least one conductive element causes local melting of the tubular member; and constraining the local melting of the tubular member to fill a transition zone adjacent the at least one conductive element with the mold.

2. The method of claim 1, wherein attaching the at least one conductive element on the tubular member comprises applying a radial force.

3. The method of claim 2, wherein applying the radial force compresses the at least one conductive element so that an outer surface of the at least one conductive element lies substantially flush with the outer wall of the tubular member.

4. The method of claim 3, further comprising swaging the at least one conductive element.

5. The method of claim 2, further comprising swaging the at least one conductive element.

6. The method of claim 1, further comprising applying a sacrificial heat-shrink member over the at least one conductive element.

7. The method of claim 1, wherein one or more electrical conductors are arranged within a lumen defined by the tubular member.

8. The method of claim 1, wherein one or more electrical conductors are arranged between an inner wall and an outer wall of the tubular member.

9. The method of claim 1, wherein the at least one conductive element includes a ring electrode snug fit about the tubular member.

10. The method of claim 1, wherein the at least one conductive element comprises a conductive ring, and further comprising, prior to the induction heating, reducing a diameter of the conductive ring after the placing on the outer wall of the tubular member to be flush with a diameter of the tubular member.

11. A method of manufacturing a catheter sheath, comprising:
providing a tubular member of non-conductive material having a proximal end and a distal end;
forming at least one opening in an outer wall of the tubular member;
attaching at least one conductive element comprising a conductive ring on the outer wall of the tubular member;
reducing a diameter of the conductive ring after the attaching on the outer wall of the tubular member to be flush with a diameter of the tubular member;
placing a sacrificial heat-shrink sleeve about the conductive ring and longitudinally adjacent outer wall of the tubular member;
heating by induction the at least one conductive element in which the induction heat is directly conducted by only the at least one conductive element, such that indirect heat from the induction heated at least one conductive element causes local melting of the tubular member; and
shrinking the heat-shrink sleeve responsive to the induction heating of the at least one conductive element and constraining the local melting of the tubular member to fill a transition zone adjacent the at least one conductive element.

12. A catheter sheath, comprising:
a tubular member of non-conductive material having a proximal end and a distal end;
at least one electrical conductor extending from the proximal end to the distal end within the tubular member;
at least one opening in an outer wall of the tubular member for accessing the at least one electrical conductor within the tubular member;
at least one conductive element on the outer wall of the tubular member, the at least one conductive element being adjacent to and surrounding the at least one opening and arranged in conductive connection with the at least one electrical conductor; and
a seal, formed by induction heating, in a transition zone along each edge of the at least one conductive element between the at least one conductive element and the tubular member, the seal comprising locally melted and re-solidified material of the tubular member, the inductively heated, locally melted material of the tubular member constrained to fill the transition zones and form the seal by a mold placed about the at least one conductive element prior to the induction heating, longitudinally adjacent the outer wall of the tubular member.

13. The catheter sheath of claim 12, wherein an outer surface of the at least one conductive element lies substantially flush with the outer wall of the tubular member.

* * * * *